(12) United States Patent
Hoffman

(10) Patent No.: US 7,127,027 B2
(45) Date of Patent: *Oct. 24, 2006

(54) DIRECT CONVERSION ENERGY DISCRIMINATING CT DETECTOR

(75) Inventor: David M. Hoffman, New Berlin, WI (US)

(73) Assignee: General Electric Company, Schenectady, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 11/275,294

(22) Filed: Dec. 22, 2005

(65) Prior Publication Data

US 2006/0104411 A1     May 18, 2006

Related U.S. Application Data

(63) Continuation of application No. 10/848,877, filed on May 19, 2004.

(51) Int. Cl.
*A61B 6/00* (2006.01)
(52) U.S. Cl. .................. 378/19; 378/98.8; 250/370.09
(58) Field of Classification Search .............. 378/19, 378/98.8; 250/370.09, 370.13, 370.06, 370.1
See application file for complete search history.

(56) References Cited

U.S. PATENT DOCUMENTS

| | | | |
|---|---|---|---|
| 6,041,097 A | 3/2000 | Roos et al. | |
| 6,473,486 B1 | 10/2002 | Hoffman | |
| 6,480,562 B1 | 11/2002 | Jiang et al. | |
| 6,480,563 B1 | 11/2002 | Hoffman et al. | |
| 6,528,795 B1 | 3/2003 | Kurfess et al. | |
| 6,654,443 B1 | 11/2003 | Hoffman | |
| 6,704,391 B1 | 3/2004 | Hoffman et al. | |
| 6,775,348 B1 | 8/2004 | Hoffman | |
| 6,891,166 B1 | 5/2005 | Brahme et al. | |
| 2002/0001365 A1* | 1/2002 | Mazor et al. | 378/89 |
| 2005/0056829 A1 | 3/2005 | Green et al. | |

* cited by examiner

*Primary Examiner*—Courtney Thomas
*Assistant Examiner*—Jurie Yun
(74) *Attorney, Agent, or Firm*—Ziolkowski Patent Solutions Group, SC; Michael A. Delle Penna; Carl B. Horton

(57) ABSTRACT

A CT detector capable of energy discrimination and direct conversion is disclosed. The detector includes multiple layers of semiconductor material with the layers having varying thicknesses. The detector is constructed to be segmented in the x-ray penetration direction so as to optimize count rate performance as well as avoid saturation.

14 Claims, 6 Drawing Sheets

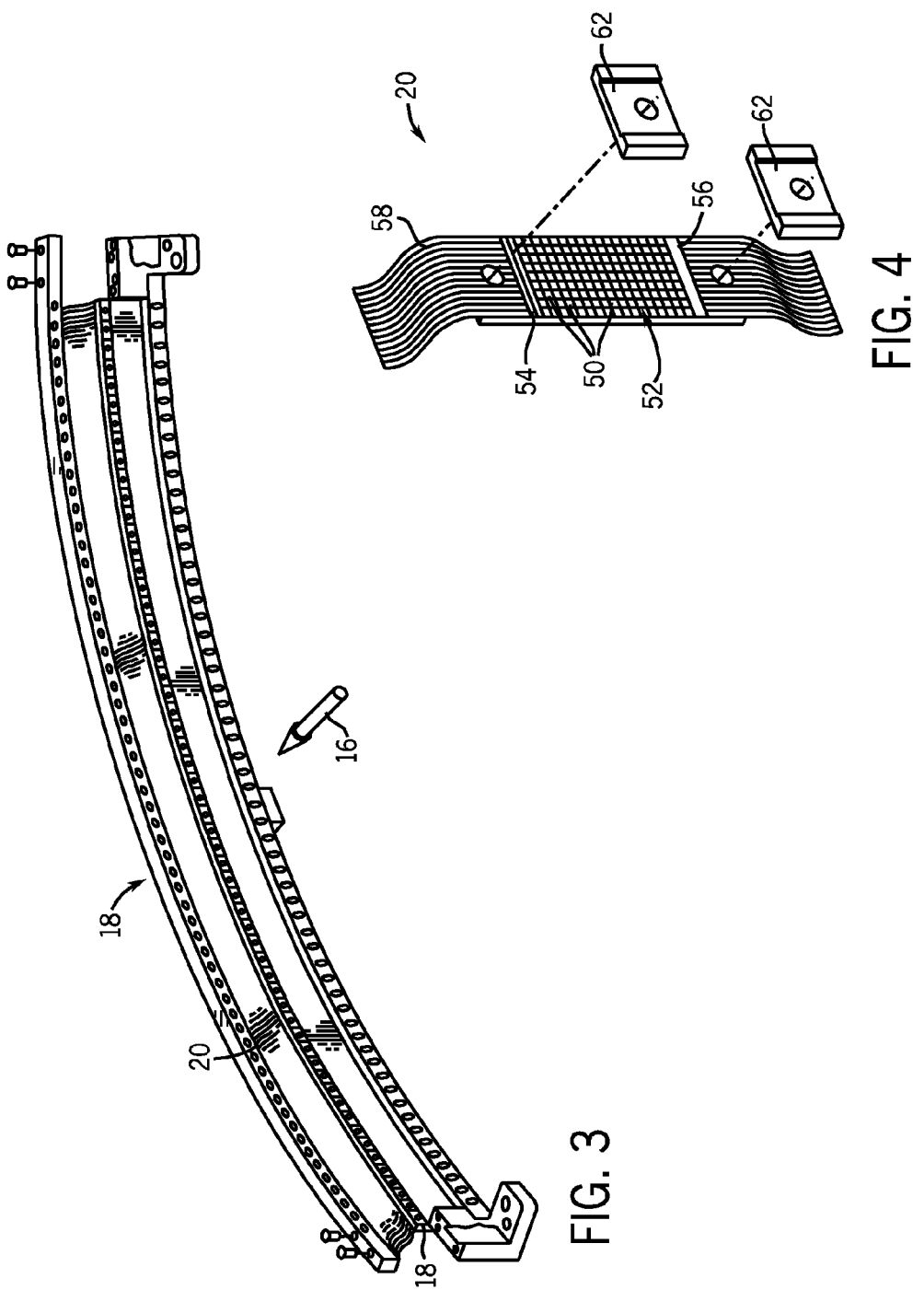

DIRECT CONVERSION ENERGY DISCRIMINATING CT DETECTOR

CROSS REFERENCE TO RELATED APPLICATIONS

The present application is continuation of and claims priority of U.S. Ser. No. 10/848,877 filed May 19, 2004, the disclosure of which is incorporated herein by reference.

BACKGROUND OF THE INVENTION

The present invention relates generally to diagnostic imaging and, more particularly, to a multi-layer direct conversion CT detector capable of providing photon count and/or energy data with improved saturation characteristics.

Typically, in radiographic imaging systems, an x-ray source emits x-rays toward a subject or object, such as a patient or a piece of luggage. Hereinafter, the terms "subject" and "object" may be interchangeably used to describe anything capable of being imaged. The beam, after being attenuated by the subject, impinges upon an array of radiation detectors. The intensity of the attenuated beam radiation received at the detector array is typically dependent upon the attenuation of the x-rays. Each detector element of the detector array produces a separate electrical signal indicative of the attenuated beam received by each detector element. The electrical signals are transmitted to a data processing system for analysis which ultimately produces an image.

In some computed tomography (CT) imaging systems, the x-ray source and the detector array are rotated about a gantry within an imaging plane and around the subject. X-ray sources typically include x-ray tubes, which emit the x-rays as a beam at a focal point. X-ray detectors typically include a collimator for collimating x-ray beams received at the detector, a scintillator for converting x-rays to light energy adjacent the collimator, and a photodiode for receiving the light energy from an adjacent scintillator and producing electrical signals therefrom. Typically, each scintillator of a scintillator array converts x-rays to light energy. Each photodiode detects the light energy and generates a corresponding electrical signal. The outputs of the photodiodes are then transmitted to the data processing system for image reconstruction.

Conventional CT imaging systems utilize detectors that convert radiographic energy into current signals that are integrated over a time period, then measured and ultimately digitized. A drawback of such detectors is their inability to provide data or feedback as to the number and/or energy of photons detected. That is, conventional CT detectors have a scintillator component and photodiode component wherein the scintillator component illuminates upon reception of radiographic energy and the photodiode detects illumination of the scintillator component and provides an electrical signal as a function of the intensity of illumination. While it is generally recognized that CT imaging would not be a viable diagnostic imaging tool without the advancements achieved with conventional CT detector design, a drawback of these detectors is their inability to provide energy discriminatory data or otherwise count the number and/or measure the energy of photons actually received by a given detector element or pixel. Accordingly, recent detector developments have included the design of an energy discriminating, direct conversion detector that can provide photon counting and/or energy discriminating feedback. In this regard, the detector can be caused to operate in an x-ray counting mode, an energy measurement mode of each x-ray event, or both.

These energy discriminating, direct conversion detectors are capable of not only x-ray counting, but also providing a measurement of the energy level of each x-ray detected. While a number of materials may be used in the construction of a direct conversion energy discriminating detector, semiconductors have been shown to be one preferred material. A drawback of direct conversion semiconductor detectors, however, is that these types of detectors cannot count at the very high x-ray photon flux rates typically encountered with conventional CT systems. The very high x-ray photon flux rate ultimately leads to detector saturation. That is, these detectors typically saturate at relatively low x-ray flux levels. This saturation can occur at detector locations wherein small subject thickness is interposed between the detector and the radiographic energy source or x-ray tube. It has been shown that these saturated regions correspond to paths of low subject thickness near or outside the width of the subject projected onto the detector fan-arc. In many instances, the subject is more or less circular or elliptical in the effect on attenuation of the x-ray flux and subsequent incident intensity to the detector. In this case, the saturated regions represent two disjointed regions at extremes of the fan-arc. In other less typical, but not rare instances, saturation occurs at other locations and in more than two disjointed regions of the detector. In the case of an elliptical subject, the saturation at the edges of the fan-arc is reduced by the imposition of a bowtie filter between the subject and the x-ray source. Typically, the filter is constructed to match the shape of the subject in such a way as to equalize total attenuation, filter and subject, across the fan-arc. The flux incident to the detector is then relatively uniform across the fan-arc and does not result in saturation. What can be problematic, however, is that the bowtie filter may not be optimum given that a subject population is significantly less than uniform and not exactly elliptical in shape. In such cases, it is possible for one or more disjointed regions of saturation to occur or conversely to over-filter the x-ray flux and create regions of very low flux. Low x-ray flux in the projection will ultimately contribute to noise in the reconstructed image of the subject.

A number of imaging techniques have been developed to address saturation of any part of the detector. These techniques include maintenance of low x-ray flux across the width of a detector array, for example, by using low tube current or current that is modulated per view. However, this solution leads to increased scanned time. That is, there is a penalty that the acquisition time for the image is increased in proportion to the nominal flux needed to acquire a certain number of x-rays that meet image quality requirements. Other solutions include the implementation of an over-range algorithm that is used to generate replacement data for the saturated data. However, these algorithms may imperfectly replace the saturated data as well as contribute to the complexity of the CT system.

It would therefore be desirable to design a direct conversion, energy discriminating CT detector that does not saturate at the x-ray photon flux rates typically found in conventional CT systems.

BRIEF DESCRIPTION OF THE INVENTION

The present invention is directed to a multilayer CT detector that can be made to perform at very high count rates that overcomes the aforementioned drawbacks.

A CT detector capable of energy discrimination and direct conversion is disclosed. The detector includes multiple layers of semiconductor material of varying thicknesses throughout the detector. In this regard, the detector is constructed so as to be segmented in the x-ray penetration direction to optimize count rate performance as well as avoid saturation.

The CT detector supports not only x-ray photon counting, but energy measurement or tagging as well. As a result, the present invention supports the acquisition of both anatomical detail as well as tissue characterization information. In this regard, the energy discriminatory information or data may be used to reduce the effects of beam hardening and the like. Further, these detectors support the acquisition of tissue discriminatory data and therefore provide diagnostic information that is indicative of disease or other pathologies. For example, detection of calcium in a plaque in a view is possible. This detector can also be used to detect, measure, and characterize materials that may be injected into a subject such as contrast agents and other specialized materials such as targeting agents. Contrast materials can, for example, include iodine that is injected into the blood stream for better visualization. A method of fabricating such a detector is also disclosed.

Therefore, in accordance with one aspect of the present invention, a direct conversion CT detector includes multiple direct conversion layers designed to directly convert radiographic energy to electrical signals representative of energy sensitive CT data. The detector also includes an electrical signal collection layer sandwiched between adjacent direct conversion layers.

In accordance with another aspect, the present invention includes a CT system having a rotatable gantry having a bore centrally disposed therein, a table movable fore and aft through the bore and configured to position a subject for CT data acquisition, and a radiographic energy projection source positioned within the rotatable gantry and configured to project radiographic energy toward the subject. The CT system also includes a detector array disposed within the rotatable gantry and configured to detect radiographic energy projected by the projection source and impinged by the subject. The detector array includes a plurality of detector cells, wherein each cell has a stacked arrangement of semiconductor layers in a direction generally that of energy projection and designed to provide energy sensitive data acquired from the subject in response to receiving radiographic energy.

According to another aspect, the present invention includes a CT detector having a first means and a second means for directly converting radiographic energy to electrical signals. The detector also has means for receiving electrical signals interstitially positioned between the first means for directly converting and the second means for directly converting.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 3 is a perspective view of one embodiment of a CT system detector assembly.

FIG. 4 is a perspective view of a CT detector.

DETAILED DESCRIPTION OF THE PREFERRED EMBODIMENT

The operating environment of the present invention is described with respect to a four-slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other radiographic energy.

Figure 1:
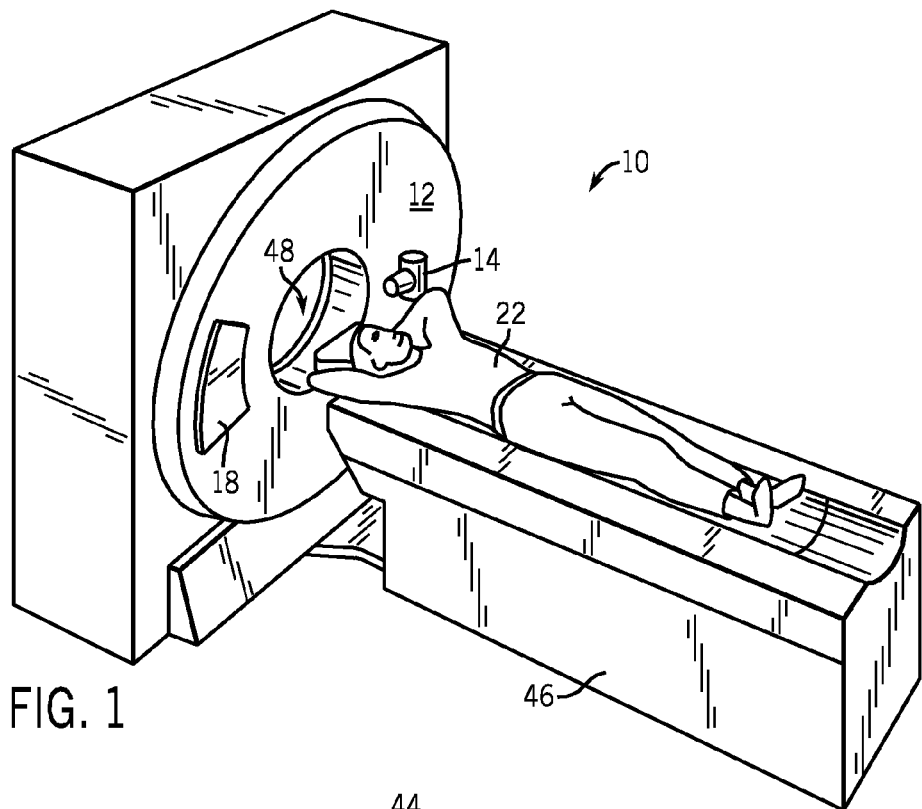
FIG. 1 is a pictorial view of a CT imaging system.
Figure 2:
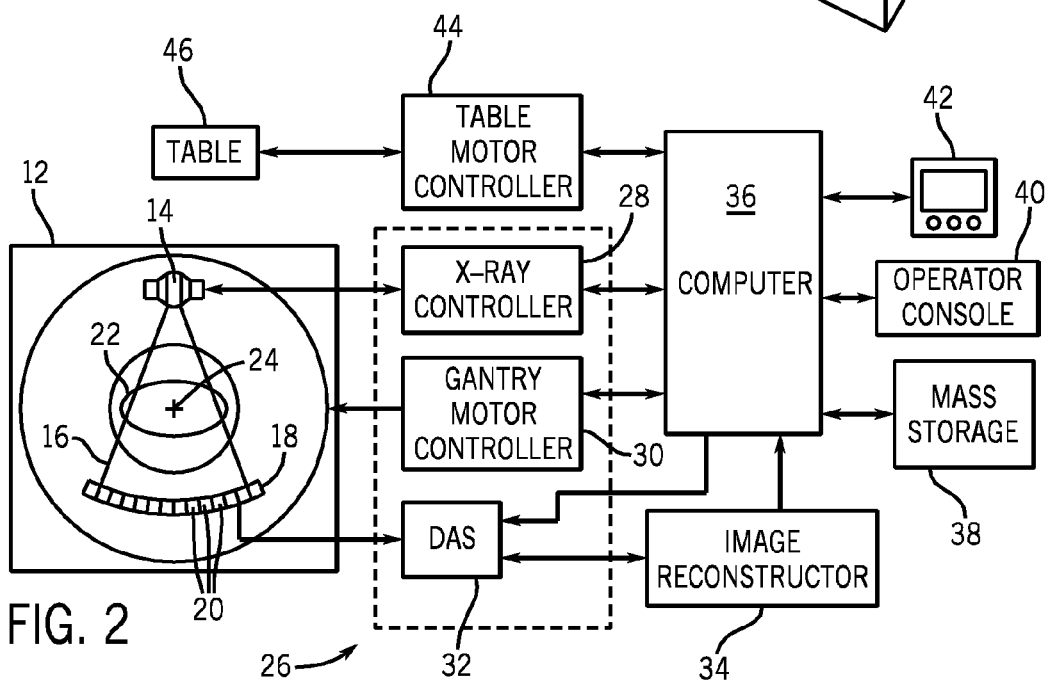
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector assembly 18 on the opposite side of the gantry 12. Detector assembly 18 is formed by a plurality of detectors 20 which together sense the projected x-rays that pass through a medical patient 22. Each detector 20 produces an electrical signal that represents not only the intensity of an impinging x-ray beam but is also capable of providing photon or x-ray count data, and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 review data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30.

In addition, computer 36 operates a table motor controller 44 which controls a motorized table 46 to position patient 22 and gantry 12. Particularly, table 46 moves portions of patient 22 through a gantry opening 48.

As shown in FIGS. 3 and 4, detector assembly 18 includes a plurality of detectors 20, with each detector including a number of detector elements 50 arranged in a cellular array. A collimator (not shown) is positioned to collimate x-rays 16 before such beams impinge upon the detector assembly 18. In one embodiment, shown in FIG. 3, detector assembly 18 includes 57 detectors 20, each detector 20 having an array size of 16×16. As a result, assembly 18 has 16 rows and 912 columns (16×57 detectors) which allows 16 simultaneous slices of data to be collected with each rotation of gantry 12.

Switch arrays 54 and 56, FIG. 4, are multi-dimensional semiconductor arrays coupled between cellular array 52 and DAS 32. Switch arrays 54 and 56 include a plurality of field effect transistors (FET) (not shown) arranged as multi-dimensional array and are designed to combine the outputs of multiple cells to minimize the number of data acquisition channels and associated cost. The FET array includes a number of electrical leads connected to each of the respective detector elements 50 and a number of output leads electrically connected to DAS 32 via a flexible electrical interface 58. Particularly, about one-half of detector element outputs are electrically connected to switch 54 with the other one-half of detector element outputs electrically connected to switch 56. Each detector 20 is secured to a detector frame 60, FIG. 3, by mounting brackets 62.

It is contemplated and recognized that for some applications, the count rate limitation of the FET arrays may make them less desirable. In this regard, as will be described, each detection pixel or cell is connected to a channel of electronics.

Switch arrays 80 and 82 further include a decoder (not shown) that enables, disables, or combines detector element outputs in accordance with a desired number of slices and slice resolutions for each slice. Decoder, in one embodiment, is a decoder chip or a FET controller as known in the art. Decoder includes a plurality of output and control lines coupled to switch arrays 54 and 56 and DAS 32. In one embodiment defined as a 16 slice mode, decoder enables switch arrays 54 and 56 so that all rows of the detector assembly 18 are activated, resulting in 16 simultaneous slices of data for processing by DAS 32. Of course, many other slice combinations are possible. For example, decoder may also select from other slice modes, including one, two, and four-slice modes.

Figure 5:
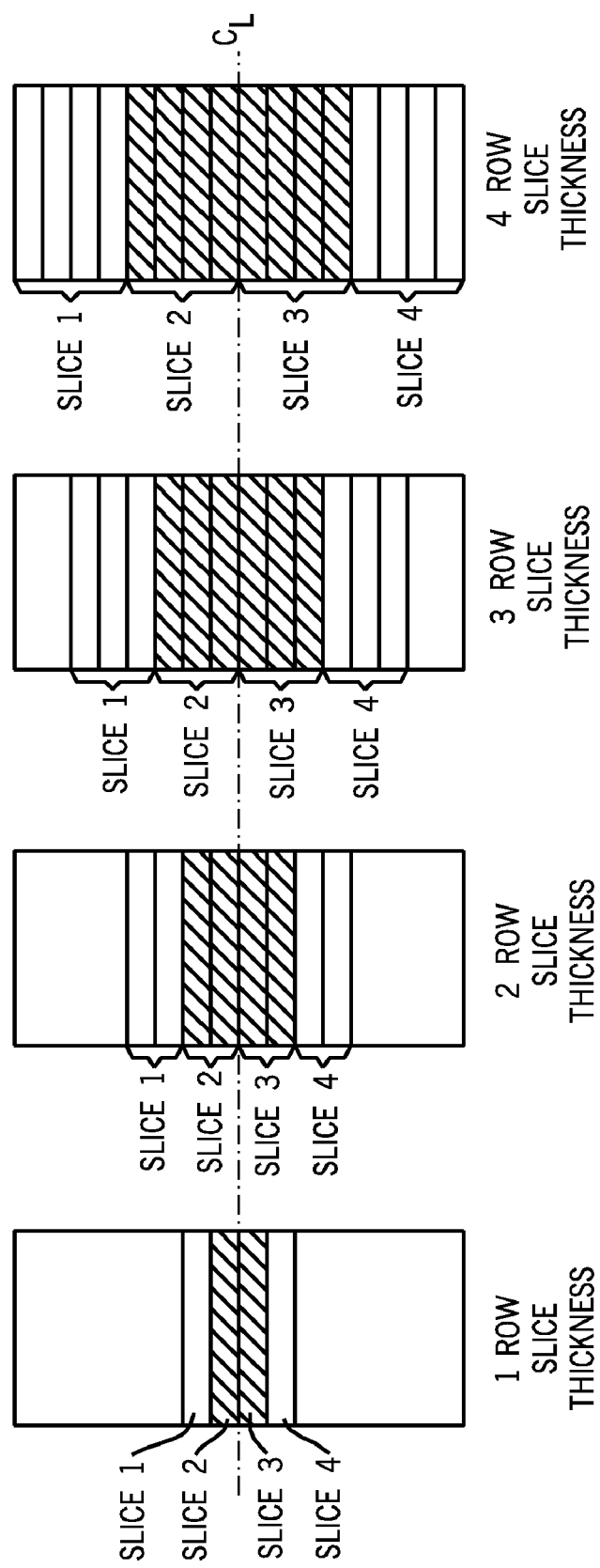
FIG. 5 is illustrative of various configurations of the detector in FIG. 4 in a four-slice mode.

As shown in FIG. 5, by transmitting the appropriate decoder instructions, switch arrays 54 and 56 can be configured in the four-slice mode so that the data is collected from four slices of one or more rows of detector assembly 18. Depending upon the specific configuration of switch arrays 54 and 56, various combinations of detectors 20 can be enabled, disabled, or combined so that the slice thickness may consist of one, two, three, or four rows of detector elements 50. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

As described above, each detector 20 is designed to directly convert radiographic energy to electrical signals containing energy discriminatory data. The present invention contemplates a number of configurations for these detectors. Notwithstanding the distinctions between each of these embodiments, each detector does share two common features. One of these features is the multilayer arrangement of semiconductor films or layers. In a preferred embodiment, each semiconductor film is fabricated from Cadmium Zinc Telluride (CZT). However, one skilled in the art will readily recognize that other materials capable of the direct conversion of radiographic energy may be used. The other common feature between the various embodiments is the use of interstitial or intervening metallized films or layers separating the semi-conducting layers. As will be described, these metallized layers are used to apply a voltage across a semiconductor layer as well as collect electrical signals from a semiconductor layer.

It is generally well known that photon count rate performance of a semiconductor is a function of the square of the thickness of the detector and the radiographic energy deposition process is exponential. The count rate performance for a CZT detector may be defined by:

$$T_{TR} = \frac{L^2}{V\mu_e}.$$

From this definition, assuming a thickness of L=0.3 cm and an electric field V of 1000 V/cm, and with a $\mu_e$ of about 1000, a maximum count rate of 1.0 megacounts may be achieved. In other words, the count rate of a CZT semiconductor layer that is 3 mm thick may have a count rate performance in the range of 1.0 megacounts/sec. However, as will be described, constructing a direct conversion semiconductor detector with multiple layers as opposed to a single thicker layer can improve count rate performance.

Figure 6:
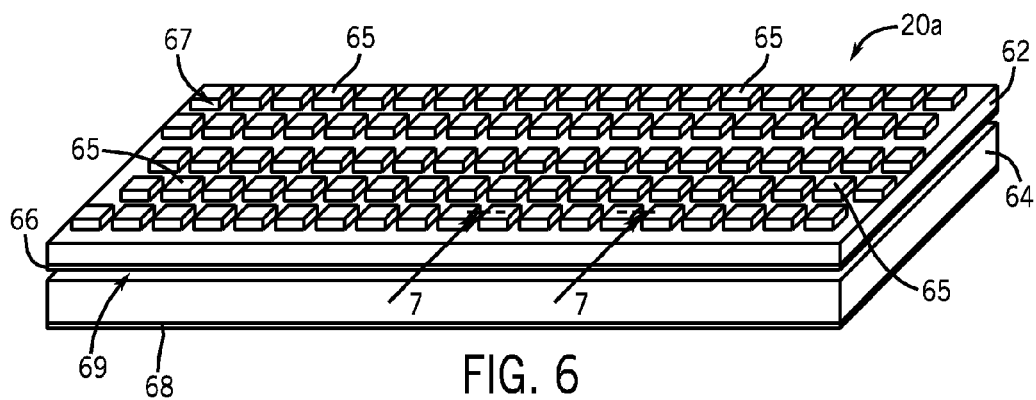
FIG. 6 is a partial perspective view of a two-layer director in accordance with the present invention.

Referring now to FIG. 6, a portion of a two-layered CZT or direct conversion detector 20a in accordance with one embodiment of the present invention is shown in perspective. Detector 20a is defined by a first semiconductor layer 62 and a second semiconductor layer 64. During the fabrication process, each semiconductor layer 62, 64 is constructed to have a number of electronically pixilated structures or pixels to define a number of detection elements 65. This electronic pixilation is accomplished by applying a 2D array 67, 69 of electrical contacts 65 onto a layer 62, 64 of direct conversion material. Moreover, in a preferred embodiment, this pixilation is defined two-dimensionally across the width and length of each semiconductor layer 62, 64.

Detector 20a includes a contiguous high voltage electrode 66, 68 for semiconductor layers 62, 64, respectively. Each high voltage electrode 66, 68 is connected to a power supply (not shown) and is designed to power a respective semiconductor layer during the x-ray or gamma ray detection process. One skilled in the art will appreciate that each high voltage connection layer should be relatively thin so as to reduce the x-ray absorption characteristics of each layer and, in a preferred embodiment, is a few hundred angstroms thick. As will be described in greater detail below, these high voltage electrodes may be affixed to a semiconductor layer through a metallization process.

Figure 7:
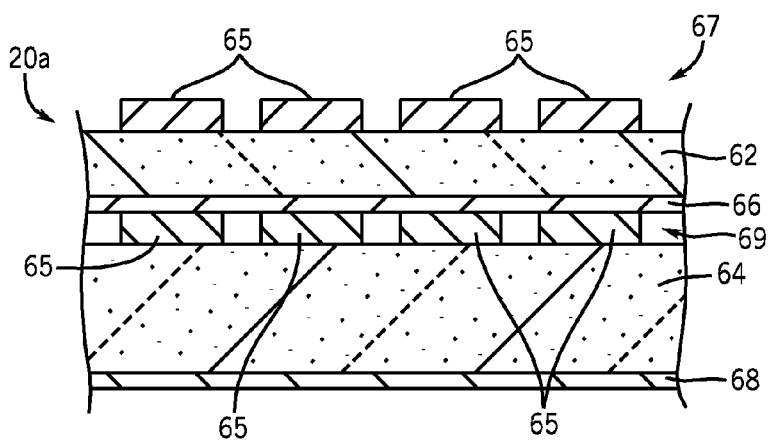
FIG. 7 is a cross-sectional view of FIG. 6 taken along lines 7—7 thereof.

Referring now to FIG. 7, a cross-sectional view of FIG. 6 taken along line 7—7 thereof illustrates the relative thickness of each semiconductor layer 62, 64. Similar to the high voltage electrode layers 66, 68, the 2D arrays 67, 69 should also be minimally absorbent of radiographic energy. Each array or signal collection layer is designed to provide a mechanism for outputting the electrical signals created by the semiconductor layers to a data acquisition system or other system electronics. One skilled in the art will appreciate that several hundred interconnects (not shown) are used to connect each contact 65 with the CT system electronics.

In addition, as shown in FIG. 7, the thickness of the semiconductor layers 62, 64 is different from one another. In this regard, more x-rays are deposited in semiconductor layer 62 than in semiconductor layer 64. For example, assuming that semiconductor layer 62 has a thickness of one millimeter (mm) and semiconductor 64 has a thickness of 2 mm, semiconductor layer 62 is expected to absorb about 78% of the x-rays whereas the second semiconductor layer 64 is expected to absorb about 22% of the x-rays. Further, it is expected that the first semiconductor layer 62 is to experience a maximum count rate that is approximately nine times faster than that of a single layer semiconductor 3 mm thick. However, the first semiconductor layer 62 measures only approximately 78% of the total flux thereby providing an 11.5 times increase in effective max count rate performance compared to a single semiconductor layer 3 mm thick. The second semiconductor layer 64 is expected to have a count rate that is 2.25 times faster than that of a single 3 mm thick semiconductor but measures only approximately 22% of the total flux, thereby, providing an equivalent or effective max count rate that is approximately 10.2 times that expected to be experienced with a single layer of 2D semiconductor material 3 mm thick. As a result of the improved count rates of the segmented detector described above relative to a single layer of semiconductor material, detector 20a may be constructed to provide a tenfold increase in count rate performance.

The above dimensions are illustrative of the improvement in maximum count rate that may be experienced with a two layer detector. However, it is contemplated that more than two layers may be used to construct a CT detector with improved count rate characteristics. For example, a single 0.43 mm layer is expected to absorb about 54% of x-rays received and, as such, has a maximum count rate of approximately 40 times that of a single layer, 3.0 mm thick semiconductor. However, a 0.43 mm layer absorbs only approximately 54% of the total flux to provide an equivalent or effective max count rate of approximately 92 times that of a single semiconductor layer that is 3 mm thick. Additional layers may be added to provide an overall count rate increase of 9200%.

Figure 8:
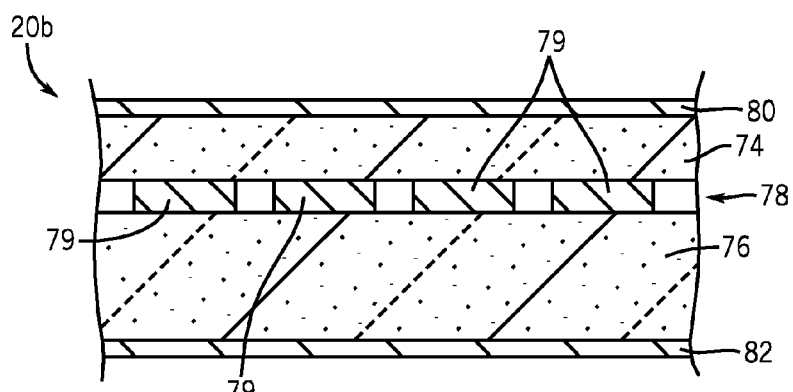
FIGS. 8–10 illustrate cross-sectional views of direct conversion detectors in accordance with several additional embodiments of the present invention.

Referring now to FIG. 8, another contemplated design for a CZT or direct conversion detector is shown. In this embodiment, detector 20b also includes a pair of semiconductor layers 74, 76. In contrast to the previously described embodiment, detector 20b includes a single, common signal collection layer or 2D contact array 78. This single, yet common array 78 is designed to collect electrical signals from both semiconductor layers 74, 76 and output those electrical signals to a DAS or other system electronics. In addition, detector 20b includes a pair of high voltage electrodes 80, 82. Each high voltage electrode effectively operates as a cathode whereas the contacts of the 2D array 78 operate as an anode. In this regard, the voltage applied via high voltage connections 80, 82 creates a circuit through each semiconductor layer to the signal collection contacts array 78.

Figure 9:
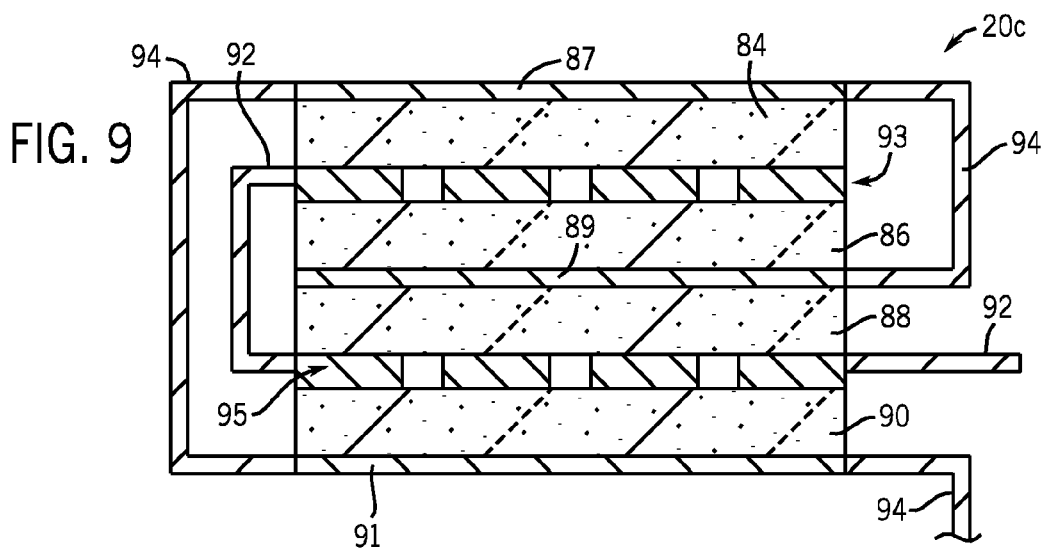

Yet another contemplated embodiment is illustrated in FIG. 9. As shown in this embodiment, detector 20c includes four semiconductor layers 84, 86, 88, and 90. Detector 20c further includes two electrically conductive lines or paths 92, 94 that are electrically connected to high voltage electrodes 87, 89, 91 as well as collection contact arrays 93, 95. Electrically conductive path 92 receives and translates electrical signals from contact arrays 93, 95. In this regard, a single data output is provided to the CT system's electronics. Similar to a single signal collection lead, a single high voltage connection 94 is used to power the four semiconductor layers 84–90 via electrodes 87, 89, 91. Detector 20c only requires a single high voltage connection.

Figure 10:
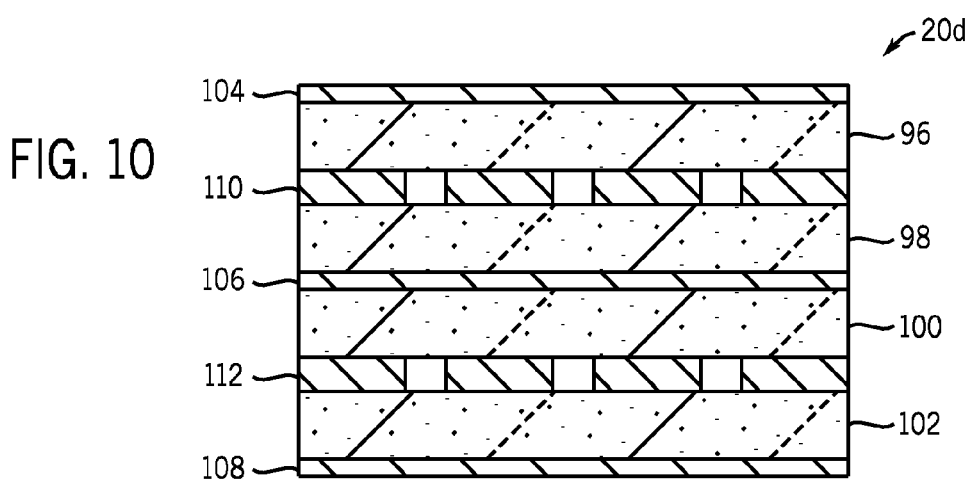

Referring to FIG. 10, a monolithic embodiment of the present invention is shown. Similar to the embodiment of FIG. 7, detector 20d includes four semiconductor layers 96–102. Each semiconductor layer 96–102 is connected to a pair of electrically conductive layers. In this regard, one electrically conductive layer is used for application of a voltage whereas the other electrically conductive layer is used for collection of the electrical signals generated by the respective semiconductor layers. To minimize the number of electrically conductive layers, detector 20d utilizes an alternating electrically conductive layer architecture. That is, every other electrically conductive layer is used for high voltage connection with the other electrically conductive layers used for signal collection. In this regard, electrically conductive layers 104, 106, and 108 are used for application of a relatively high voltage whereas layers 110 and 112 include contacts for signal collection. As such, high voltage collection layers 104 and 108 are used to apply a voltage to semiconductor layers 96 and 102, respectively. High voltage connection layer 106 is used to apply a voltage to semiconductor layers 98 and 100.

As described above, in a preferred embodiment, each semiconductor layer is constructed from CZT material. One skilled in the art will appreciate that there are a number of techniques that may be used to construct such a semiconductor. For example, molecular beam epitaxy (MBE) is one method that may be used to grow each thin layer of CZT material. One skilled in the art will appreciate that a number of techniques may be used to metallize the semiconductor layers to provide the electrically conductive connections heretofore described.

Figure 11:
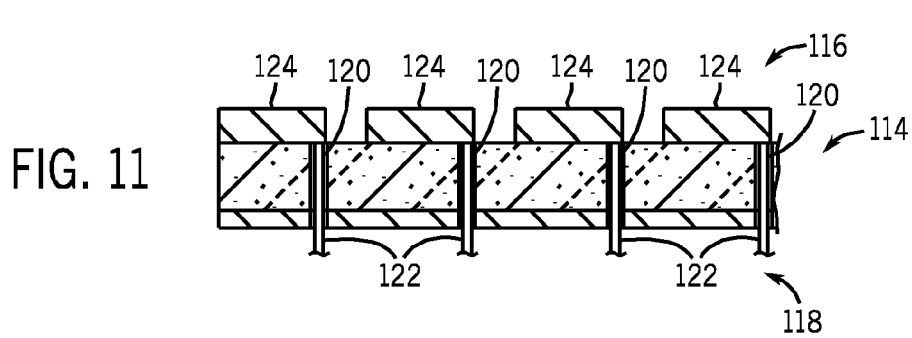
FIG. 11 is a cross-sectional schematic view of that shown in FIG. 10 illustrating signal feedthroughs that are created in another embodiment of the invention.

Further, metallization may also be used to provide signal feedthroughs for the collection contacts as illustrated in FIG. 11. As shown, a single layer of semiconductor material 114 is sandwiched between an array 116 of collection contacts and a high voltage electrode layer 118. Prior to metallization of the semiconductor layer 114 to form collection contact array 116 and high voltage electrode layer 118, holes 120 may be etched or otherwise formed in semiconductor 114. The holes 120 may then be metallized to provide a signal feed path 122 from a respective collection contact 124. The signal feedthroughs or conductive paths 122 are constructed within holes 120 so as to not be in contact with the near-contiguous high voltage electrode layer 118. In this regard, signal runs may extend vertically or in the x-ray reception direction throughout the detector to a bus (not shown) designed to translate the electrical signals emitted by the individual collection contacts 124 to the CT system's electronics. As a result, a stacked arrangement of a series of thin stacked layers in the x-ray direction is formed.

Figure 12:
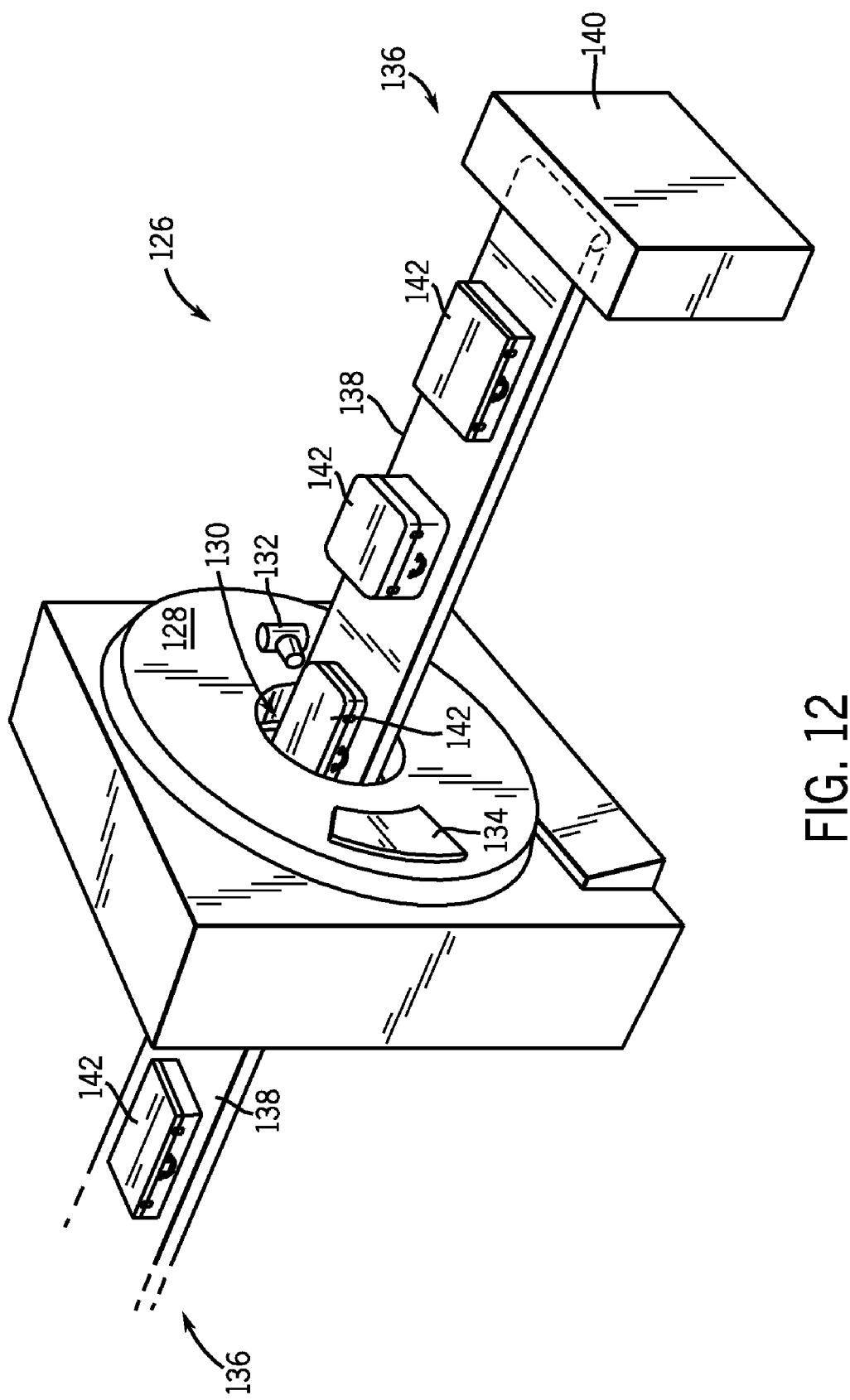
FIG. 12 is a pictorial view of a CT system for use with a non-invasive package inspection system.

Referring now to FIG. 12, package/baggage inspection system 126 includes a rotatable gantry 128 having an opening 130 therein through which packages or pieces of baggage may pass. The rotatable gantry 128 houses a high frequency electromagnetic energy source 132 as well as a detector assembly 134. A conveyor system 136 is also provided and includes a conveyor belt 138 supported by structure 140 to automatically and continuously pass packages or baggage pieces 142 through opening 130 to be scanned. Objects 142 are fed through opening 130 by conveyor belt 138, imaging data is then acquired, and the conveyor belt 138 removes the packages 142 from opening 130 in a controlled and continuous manner. As a result, postal inspectors, baggage handlers, and other security personnel may non-invasively inspect the contents of packages 142 for explosives, knives, guns, contraband, etc.

Therefore, a direct conversion CT detector includes multiple direct conversion layers designed to directly convert radiographic energy to electrical signals representative of energy sensitive CT data. The detector also includes an electrical signal collection layer sandwiched between adjacent direct conversion layers.

The present invention also includes a CT system having a rotatable gantry having a bore centrally disposed therein, a table movable fore and aft through the bore and configured to position a subject for CT data acquisition, and a radiographic energy projection source positioned within the rotatable gantry and configured to project radiographic energy toward the subject. The CT system also includes a detector array disposed within the rotatable gantry and configured to detect radiographic energy projected by the projection source and impinged by the subject. The detector array includes a plurality of detector cells, wherein each cell has a stacked arrangement of semiconductor layers in a direction generally that of energy projection and designed to provide energy sensitive data acquired from the subject in response to receiving radiographic energy.

The present invention further includes a CT detector having a first means and a second means for directly converting radiographic energy to electrical signals. The detector also has means for receiving electrical signals interstitially positioned between the first means for directly converting and the second means for directly converting.

The present invention has been described in terms of the preferred embodiment, and it is recognized that equivalents, alternatives, and modifications, aside from those expressly stated, are possible and within the scope of the appending claims.

What is claimed is:

1. A CT detector comprising:
    a first semiconductor layer spaced apart from a second semiconductor layer, the semiconductor layers designed to convert x-rays to electrical signals and collectively having a max photon count rate that is greater than a single semiconductor layer having a thickness equal to a composite thickness of the first and the second semiconductor layers;
    a readout layer sandwiched between the first and the second semiconductor layers, the readout layer designed to translate the electrical signals to a data acquisition system.

2. The CT detector of claim 1 further comprising a voltage application layer positioned adjacent to a surface of each semiconductor layer opposite to that which the readout layer is positioned.

3. The CT detector of claim 2 wherein each semiconductor layer is in contact with a readout layer and a voltage application layer.

4. The CT detector of claim 1 wherein the semiconductor layers are formed of at least CZT.

5. The CT detector of claim 1 wherein the semiconductor layers are arranged in a layered stack in an x-ray penetration direction.

6. The CT detector of claim 5 wherein the first semiconductor layer absorbs more x-rays than the second semiconductor layer which is positioned farther from an x-ray source.

7. The CT detector of claim 1 wherein the semiconductor layers have the same thickness.

8. The CT detector of claim 1 wherein the first semiconductor layer is thicker than the second semiconductor layer.

9. The CT detector of claim 1 wherein the readout layer reads out electrical signals from both semiconductor layers.

10. A CT detector comprising:
    a stacked arrangement of direct conversion layers aligned to directly convert x-rays to electrical signals;
    the stacked arrangement including a first direct conversion layer and a second direct conversion layer spaced apart from one another by a shared readout layer;
    the first direct conversion layer more absorbent of x-rays than the second direct conversion layer.

11. The CT detector of claim 10 wherein the readout layer carries energy-sensitive CT data from the first and the second direct conversion layers to a data acquisition system.

12. The CT detector of claim 11 wherein the energy-sensitive CT data includes photon count and energy level information.

13. The CT detector of claim 10 wherein the stacked arrangement further includes a pair of biasing layers, each biasing layer connected to a respective direct conversion layer and designed to create a potential across a direct conversion layer with the shared readout layer.

14. The CT detector of claim 13 wherein the readout layer and the biasing layers are metallized to a respective surface of the first and the second direct conversion layers.

* * * * *